United States Patent
Jensen (10) Patent No.: US 11,346,766 B2
(45) Date of Patent: May 31, 2022

(54) MONITORING STEEL SUPPORT STRUCTURES FOR OFFSHORE WIND TURBINES

(71) Applicant: Ørsted Wind Power A/S, Fredericia (DK)

(72) Inventor: Birit Buhr Jensen, Gentofte (DK)

(73) Assignee: Ørsted Wind Power A/S

( * ) Notice: Subject to any disclaimer, the term of this patent is extended or adjusted under 35 U.S.C. 154(b) by 94 days.

(21) Appl. No.: 16/492,037

(22) PCT Filed: Mar. 7, 2018

(86) PCT No.: PCT/EP2018/055640
§ 371 (c)(1),
(2) Date: Sep. 6, 2019

(87) PCT Pub. No.: WO2018/162573
PCT Pub. Date: Sep. 13, 2018

(65) Prior Publication Data
US 2021/0140872 A1   May 13, 2021

(30) Foreign Application Priority Data
Mar. 8, 2017   (EP) .................................... 17159850

(51) Int. Cl.
G01N 17/04     (2006.01)
G01N 33/208    (2019.01)
G01N 27/04     (2006.01)

(52) U.S. Cl.
CPC ............. G01N 17/04 (2013.01); G01N 27/04 (2013.01); G01N 33/208 (2019.01)

(58) Field of Classification Search
CPC ....... G01N 33/20; G01N 33/208; G01N 27/04
See application file for complete search history.

(56) References Cited

U.S. PATENT DOCUMENTS

| 4,677,373 A | 6/1987 | Kobayashi et al. |
| 2004/0176934 A1 | 9/2004 | Kihira et al. |

(Continued)

FOREIGN PATENT DOCUMENTS

| EP | 2124034 A1 | 11/2009 |
| EP | 2894466 A1 | 7/2015 |

(Continued)

OTHER PUBLICATIONS

Troels, et al., "Monitoring and Inspection Options for Evaluating Corrosion in Offshore Wind Foundations", NACE International Corrosion Conference Proceedings, Paper 7702, Denmark, Mar. 6, 2016, 11 pages.

*Primary Examiner* — Noam Reisner
(74) *Attorney, Agent, or Firm* — Condo Roccia Koptiw LLP (57) ABSTRACT

Disclosed is a method for estimating deterioration of a steel support structure (180) supporting an offshore wind turbine (181). The steel support structure (180) being made of a first type of steel, the method comprising the steps of: (a) providing a first sensor (111) having one or more sensor elements, wherein a first sensor element of the one or more sensor elements is made of a type of steel corresponding to the first type of steel; (b) arranging the first sensor (111) in connection with said steel support structure (180); (c) inducing an electrical current through at least one of the one or more sensor elements; (d) monitoring the deterioration of a part of the first sensor (111) by in a first time interval measuring electrical properties of the first sensor (111) and storing the measurements as first data; (e) estimating the deterioration of the steel support structure (180) from the first data.

20 Claims, 5 Drawing Sheets

(56) References Cited

U.S. PATENT DOCUMENTS

| | | | |
|---|---|---|---|
| 2011/0012628 A1* | 1/2011 | Dobashi | G01N 17/02 |
| | | | 324/700 |
| 2012/0280849 A1 | 11/2012 | Chang et al. | |
| 2012/0282035 A1 | 11/2012 | Ebert | |
| 2014/0069810 A1 | 3/2014 | Tachibana et al. | |
| 2015/0247815 A1 | 9/2015 | Chen et al. | |
| 2016/0041113 A1* | 2/2016 | Pagani | G01N 27/223 |
| | | | 324/694 |
| 2017/0343514 A1 | 11/2017 | Takata et al. | |

FOREIGN PATENT DOCUMENTS

| | | |
|---|---|---|
| EP | 3101411 A1 | 12/2016 |
| EP | 2615226 B1 | 9/2017 |
| JP | S62-19748 A | 1/1987 |
| JP | H01-267447 A | 10/1989 |
| JP | 2012-077601 A | 4/2012 |
| JP | 2013-509520 A | 3/2013 |
| JP | 2014-052279 A | 3/2014 |
| TW | 531637 B | 5/2003 |
| TW | 201245748 A | 11/2012 |
| WO | 2013/068739 A2 | 5/2013 |
| WO | 2016/114136 A1 | 7/2016 |

* cited by examiner

MONITORING STEEL SUPPORT STRUCTURES FOR OFFSHORE WIND TURBINES

CROSS REFERENCE TO RELATED APPLICATIONS

This application is the National Stage Entry under 35 U.S.C. § 371 of Patent Cooperation Treaty Application No. PCT/EP2018/055640, filed Mar. 7, 2018, which claim priority from European Patent Application No. 17159850.1, filed Mar. 8, 2017, the contents of which are hereby incorporated by reference herein.

FIELD

The present invention relates to a method for estimating deterioration of a steel support structure supporting an offshore wind turbine.

BACKGROUND

Offshore wind has proven to be an effective way of producing electricity. It is however challenging to provide a secure foundation for supporting the wind turbine. The task is not made easier by the fact that the requested lifetime of the foundation typically is more than 25 years.

Steel support structures are commonly used to support offshore wind turbines. The steel support structures are however deteriorated in a number of ways. One of the most critical being corrosion. Seawater, compared to fresh water increases the corrosion rate. Salts in seawater (electrolyte) increases the conductivity of the electrolyte. To account for the corrosion, the amount of steel used for the steel support structures is typically increased, coatings are applied to the surfaces and cathodic protection is applied. Increasing the amount of steel, applying coating and using cathodic protection do however increase the cost of the steel support structures.

It remains a problem to provide a method for more precisely estimating deterioration of steel support structures supporting offshore wind turbines

SUMMARY

According to a first aspect, the invention relates to a method for estimating deterioration of a steel support structure supporting an offshore wind turbine, said steel support structure being made of a first type of steel, said method comprising the steps of:
(a) providing a first sensor having one or more sensor elements, wherein a first sensor element of said one or more sensor elements is made of a type of steel corresponding to said first type of steel;
(b) arranging said first sensor in connection with said steel support structure;
(c) inducing an electrical current through at least one of said one or more sensor elements;
(d) monitoring the deterioration of a part of said first sensor by in a first time interval measuring electrical properties of the first sensor and storing the measurements as first data;
(e) estimating the deterioration of said steel support structure from said first data.
Consequently, by using a sensor having a sensor element made of a type of steel corresponding to the steel of the steel support structure, a simple and precise method of estimating deterioration of a steel support structure is provided.

The steel support structure may be a foundation monopile, a space frame structure e.g. a jacket or a tripod, a compliant tower, a gravity structure or a floating structure for an offshore structure such as a TLP (tension leg platform), a Semi-Submersible, a spar platform or a tri-pile. The first sensor may be configured to detect general corrosion, pitting corrosion, and or the deterioration of a coating. The steel support structure may comprise a transition piece.

The first sensor may be arranged on the steel support structure, in the steel support structure, fixed to the steel support structure, or fixed to the seabed close to the steel support structure. The first sensor may be arranged on the exterior of the steel support structure or in a hollow interior of the steel support structure. The first sensor may be arranged below the sea surface, in the seabed, in the tidal zone, in the splash zone, or in the atmospheric zone. The first sensor may be secured to a fixation element wherein the fixation element is secured to the steel support structure.

The electrical current may be induced through the first sensor element or another sensor element of the first sensor. The electrical current may enter the sensor element through a first electrical terminal connected to a first side of the sensor element and exit the sensor element through a second electrical terminal connected to a second side of the sensor element. Alternatively/additionally, the electrical current may enter the sensor element through an electrical terminal and exit the sensor element through an outer surface facing the water or the seabed, or enter the sensor element through the outer surface and exit the sensor element through an electrical terminal. The exterior surface may be treated in a manner similar to the manner the steel support structure is treated e.g. coated with the same coating or a similar coating and/or sandblasted in the same way. The electrical current may be a DC current or an AC current. The current may be supplied to the first sensor from a battery forming part of the first sensor, or an external power source connected to the first sensor via power cables e.g. an external battery, the power grid, or the generator of the wind turbine. The current may be fixed and have a known size. Alternatively, the power source may provide a fixed voltage of a known size whereby the electrical current is a function of the impedance/resistivity of at least one sensor element.

The first time interval may be at least 1 week, 1 month, 6 months, 1 year, 2 years, 5 years 10 years, 15 years, 20 years, or 25 years. The first time interval may be less than 1 year, 2 years, 5 years 10 years, 15 years, 20 years, or 25 years. The electrical properties may be measured periodically e.g. at least once pr. second, minute, hour, day, or week.

The measured electrical properties of the first sensor may be: the voltage drop over the first sensor element or another sensor element, the current through the first sensor element or another sensor element, the voltage drop between two sensor elements, or a sensor element and reference electrode. The first sensor may comprise a processing unit configured to measure the electrical properties. The first sensor may be configured to estimate corrosion of the first sensor element or another sensor element e.g. the first sensor may be an electrical resistance (ER) corrosion probe. Alternatively/additionally, the first sensor may be configured to estimate the deterioration of a coating applied to the first sensor element or another sensor element.

The deterioration of the steel support structure may be estimated by assuming that deterioration of the steel support structure corresponds substantially to the deterioration of said first sensor element. The first data may be processed using a processing unit to estimate the deterioration of the steel support structure. The processing unit may be arranged in the first sensor, separate from the first sensor but arranged in connection with the steel support structure, or separate from the steel support structure e.g. the first data may be transferred to the processing unit over WAN such as the internet.

The first sensor element may be made substantially at the same time and at the same production facility as the steel support structure. This may ensure that the properties of the steel of the first sensor element are similar to the properties of the steel of the steel support structure.

In some embodiments step (a) further comprises providing a second sensor, said second sensor comprising a Zn reference electrode, and wherein step (b) further comprises embedding said second sensor in the seabed. Consequently, by using a Zn reference electrode, the electrode may be better adapted to the special environment present in the seabed. Thus the Zn reference electrode may provide more reliable measurements compared to measurements provided by a Ag/AgCl reference electrodes.

The second sensor may be embedded in the seabed or where seabed sedimentation is likely to occur in time or in the water. The reference electrode may be used to measure structure to electrolyte potential as a voltage difference between a structure connection and the reference electrode. Also the potential difference between more than one reference electrodes (Zn, Ag/AgCl or other) can be measured to evaluate gradients in the water, in the seabed or between water and seabed.

In some embodiments said steel support structure is coated on a first surface with a first type of coating, the first sensor element is coated with said first type of coating, and wherein step (c) further comprises inducing a current through said first sensor element, step (d) further comprises measuring changes in the electrical properties of said first sensor element, and step (e) further comprises estimating the deterioration of the coating of said steel support structure from said first data.

Consequently, a simple and effective method of estimating the deterioration of the coating of a steel support structure is provided.

The first sensor may be arranged in proximity of the coated first surface of the steel support structure. The entire first sensor element or only a part of the first sensor element may be coated. The first sensor element may have an exterior surface facing the water/atmosphere or the seabed wherein the exterior surface may be coated. The exterior surface may be planar or have a curvature matching the curvature of the steel support structure. The coating may be solvent free or high solids epoxy paints in different layer thicknesses and in different number of layers, with and without topcoat (polyurethane or polysiloxane).

In some embodiments step (d) comprises inducing an electrical current between said first sensor element and an reference electrode through the water or the seabed i.e. through the electrolyte, estimating the electrical impedance between the first sensor element and the reference electrode, and wherein step (e) further comprises estimating the deterioration of the coating of said steel support structure by analysing the first data to estimate the change over time of the electrical impedance between the first sensor element and the reference electrode.

The coatings typically used functions as electrical insulators. Thus, by analysing the change in electrical impedance e.g. over a range of frequencies, the deterioration may be estimated e.g. a fall in the electrical impedance is indicative of a deterioration of the coating.

The estimated deterioration may be an estimate of the absolute thickness/state of the coating or a relative estimated deterioration. The correlation between the change over time of the electrical impedance and the deterioration of the coating may be found by making inspections (non-destructive or destructive) of a suitable number of steel support structures fitted with sensors according to the present invention.

In some embodiments step (e) further comprises estimating the point in time (T1) where the coating has deteriorated to a particular point.

The particular point may be an absolute parameter value or a relative parameter value. The parameter value may be indicative of the coating's ability to protect against-corrosion. The particular point may be when the coating has stopped to protect the steel support structure against corrosion or only has a particular percentage of its original protective capabilities left. A curve fit may be used to find T1 e.g. a curve may be fitted to the first data and used to predict T1, as explained in relation to FIG. 11.

In some embodiments the method further comprises the step of: (f) applying additional anti-corrosion protection to said steel support structure at a point in time (T2) where (T2) is selected dependent on (T1).

Consequently, additionally anti-corrosion protection may be applied at the point in time where it is needed.

In some embodiments the anti-corrosion protection is a cathodic protection system.

In some embodiments the anti-corrosion protection is a new coating.

In some embodiments step (a) further comprises:
providing a second sensor having one or more sensor elements, wherein a first sensor element of said one or more sensor elements is made of a conductive material e.g. a metal and coated with a second type of coating;
wherein step (b) further comprises:
arranging said second sensor in connection with said steel support structure;
wherein step (c) further comprises:
inducing an electrical current through said first sensor element of said second sensor;
wherein step (d) further comprises:
monitoring the deterioration of the coating of said first sensor element of said second sensor in a first time interval by measuring electrical properties of the first sensor element and storing the measurements as second data;
wherein step (e) further comprises
estimating the deterioration of the coating of said steel support structure from both said first data and said second data.

Consequently, by using two sensor deterioration of different parts of the steel support structure may be estimated.

In some embodiments the second type of coating is identical to the first type of coating; or
wherein the second type of coating is different from the first type of coating and the steel support structure is coated on a second surface with the second type of coating.

In some embodiments the steel support structure has a wall surrounding a hollow interior and wherein the steel support structure has a first opening in the wall forming a passage from the hollow interior to the exterior and wherein step (b) comprises arranging the first sensor in the first opening.

Consequently, the first sensor may be effectively protected. Placing the first sensor in an opening may, furthermore, secure that the first sensor is exposed to local conditions mimicking the conditions that the steel support structure is exposed to e.g. if the first sensor is attached to the exterior of the steel support structure special flow conditions may be created around the sensor that potentially can change the manner of which the first sensor element is deteriorated.

In some embodiments the first sensor is arranged inside the first opening in a manner whereby no part of the first sensor extends out of the first opening and into the exterior.

In some embodiments the first sensor is arranged inside the first opening before the steel support structure has been secured to the seabed, the first opening being formed in a part of the steel support structure that is inserted into the seabed, the steel support structure is subsequently secured to the seabed whereby the first sensor is arranged in the seabed and can provide measurements indicative of deterioration of the part of the steel support structure inserted into the seabed.

Consequently, the first sensor may provide measurements indicative of deterioration of the part of the steel support structure inserted into the seabed.

In some embodiments the first sensor is secured to a fixation element, and wherein the fixation element is inserted into the first opening.

The use of a fixation element makes it possible to use the same type of sensor for different steel support structures and/or at different locations on a steel support structure. This lowers cost and improves reliability.

The use of fixation element, furthermore, may help to secure that a tight fit is formed between the first opening and fixation element, whereby an exchange of water between interior and exterior of the steel support structure can be prevented.

In some embodiments the first opening and the fixation element have a circular or oval shape.

This may make it easier to make the first opening without significantly reducing the strength of the first steel support structure.

In some embodiments a plurality of sensors are secured to the fixation element.

In some embodiments, the first sensor element faces the exterior and one or more power or control cables are connected to the first sensor, the one or more power or control cables being arranged inside the hollow interior of the steel support structure.

Consequently, the power or control cables may be effectively protected.

In some embodiments the one or more power or control cables are connected to the first sensor before the steel support structure is secured to the seabed, and wherein a protective element protrudes from the inner wall of the hollow interior below the first opening, said protective element being configured to protect the one or more power or control cables when the steel support structure is inserted into the seabed.

In some embodiments said first sensor further comprises a second sensor element, a first electrical insulator, and a second electrical insulator, wherein said second sensor element is separated from said first sensor element by said first electrical insulator; said second electrical insulator and said first sensor element together encapsulate said second sensor element and the first electrical insulator and protect the second sensor element and the first electrical insulator from coming into contact with the water; said first electrical insulator is configured to either break down, dissolve, and/or lower its electrical impedance when it comes into contact with water, whereby the electrical impedance between the first sensor element and the second sensor element is lowered after corrosion has formed a pinhole in the first sensor element allowing the water to come into contact with the first electrical insulator; and wherein step (e) comprises processing said first data to estimate the point in time T3 when a pinhole was formed in the first sensor element.

Consequently, the degree of pitting corrosion may be estimated. As pitting corrosion often constitutes a more significant problem than uniform corrosion, this information may be very valuable.

The first sensor may further be configured to detect the average corrosion whereby the degree of pitting corrosion relative to the average corrosion may be determined. The first electrical insulator may be a fluid or a powder having an electrical resistivity being higher than the electrical resistivity of the water surrounding the steel support structure e.g. purified water or atmospheric air. Alternatively, the first electrical insulator may be a sponge. The sponge may be made of a laboratory grade filter. The second electrical insulator should be made of a material that corrodes/deteriorates substantially slower than the first sensor element. The second electrical insulator may be made of an epoxy. The second electrical insulator may partly be formed by the housing of the first sensor.

In some embodiments step (d) comprises measuring at a plurality of points in time either:
  the electrical impedance of the second sensor element;
  the electrical impedance between the second sensor element and a reference electrode separated from the second sensor element at least by the first electrical insulator; or
  the electrical impedance between a first electrical terminal connected to a first end of the first sensor element and a second electrical terminal connected to a second end of the first sensor element;
wherein T3 is estimated by processing the plurality of estimated electrical impedances.

The reference electrode may be ground electrode e.g. the first sensor may comprise a structure connection whereby the steel support structure functions as a ground electrode.

After a pinhole has been formed in the first sensor element, water will come into contact with the second sensor element. This may result in three effects.

Firstly, the impedance between the second sensor element and a reference electrode separated from the second sensor element at least by the first electrical insulator will decrease as the insulating properties of the first electrical insulator will decrease. The first sensor element may function as the reference electrode. Alternatively, the first sensor may comprise a dedicated reference electrode.

Figure 6A:
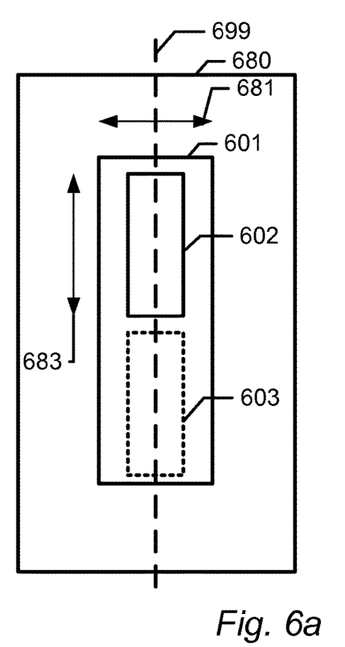
FIGS. 6a-b show schematic drawings of a sensor arranged on a wall of a steel support structure supporting an offshore wind turbine, according to an embodiment of the invention.
Figure 6B:
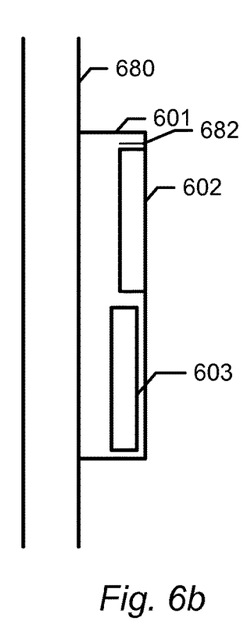

Secondly, the second sensor element will start to corrode. This corrosion may be determined by measuring an increase in the impedance of the second sensor element, i.e. similar to what is explained in relation to FIGS. 6-7.

Thirdly, the impedance between a first electrical terminal connected to a first end of the first sensor element and a second electrical terminal connected to a second end of the first sensor element will fall as the first electrical insulator will start to function as an electrolytical connection.

Thus, by monitoring the first sensor to detect at least one of the three effects T3 may be determined.

In some embodiments T3 is estimated as the point in time where the electrical impedance or an estimated rate of change of the electrical impedance reaches or exceeds a predetermined threshold.

According to a second aspect, the invention relates to a method for estimating deterioration of a steel support structure supporting an offshore wind turbine, said steel support structure being coated on a first surface with a first type of coating, said method comprising the steps of:
(a) providing a first sensor having one or more sensor elements, wherein a first sensor element of said one or more sensor elements is made of a metal and coated with the first type of coating;
(b) arranging said first sensor in connection with said steel support structure;
(c) inducing an electrical current through said first sensor element;
(d) monitoring the deterioration of the coating of said first sensor element in a first time interval by measuring electrical properties of the first sensor element and storing the measurements as first data;
(e) estimating the deterioration of the coating of said steel support structure from said first data.

Consequently, a simple and effective method of estimating the deterioration of the coating of a steel support structure is provided.

According to a third aspect, the invention relates to a method for estimating deterioration of a steel support structure supporting an offshore wind turbine, wherein the steel support structure has a wall surrounding a hollow interior, the wall has a first opening forming a passage from the hollow interior to the exterior, said method comprising the steps of:
(a) providing a first sensor having one or more sensor elements, wherein a first sensor element of said one or more sensor elements is made of a metal;
(b) arranging said first sensor in said first opening of said steel support structure;
(c) inducing an electrical current through at least one of said one or more sensor elements;
(d) monitoring the deterioration of a part of said first sensor or directly the deterioration of the steel support structure by in a first time interval measuring electrical properties of the first sensor and storing the measurements as first data;
(e) estimating the deterioration of said steel support structure from said first data.

Consequently, the first sensor may be effectively protected. Placing the first sensor in an opening may, furthermore, secure that the first sensor is exposed to local conditions mimicking the conditions that the steel support structure is exposed to e.g. if the first sensor is attached to the exterior of the steel support structure special flow conditions may be created around the sensor that potentially can change the manner of which the first sensor element is deteriorated.

The first senor may be an electrical resistance (ER) corrosion probe. Alternatively, the first sensor may comprise a reference electrode e.g. a Zn reference electrode and be used to measure structure to electrolyte potential as a voltage difference between a structure connection and the reference electrode. Also the potential difference between more than one reference electrodes (Zn, Ag/AgCl or other) can be measured to evaluate gradients in the water, in the seabed or between water and seabed.

According to a fourth aspect, the invention relates to a method for estimating deterioration of a steel support structure supporting an offshore wind turbine, said method comprising the steps of:
(a) providing a first sensor comprising a first sensor element, a second sensor element, a first electrical insulator, and a second electrical insulator, wherein said first sensor element is made of a metal; said second sensor element is separated from said first sensor element by said first electrical insulator; said second electrical insulator and said first sensor element together encapsulate said second sensor element and the first electrical insulator and protect the second sensor element and the first electrical insulator from coming into contact with the water; said first electrical insulator is configured to either breakdown, dissolve, and/or lower its electrical impedance when it comes into contact with water, whereby the electrical impedance between the first sensor element and the second sensor element is lowered after corrosion has formed a pinhole in the first sensor element allowing the water to come into contact with the first electrical insulator;
(b) arranging said first sensor in connection with said steel support structure;
(c) inducing an electrical current through said first sensor element and/or said second sensor element;
(d) monitoring the deterioration of said first sensor element by in a first time interval measuring electrical properties of the first sensor and storing the measurements as first data;
(e) estimating the deterioration of said steel support structure from said first data by processing said first data to estimate the point in time T3 when a pinhole was formed in the first sensor element.

Consequently, the degree of pitting corrosion may be estimated. This may be very important as pitting corrosion often constitutes a more significant problem than uniform corrosion where fatigue is the design driver rather than ultimate limit state (ULS).

According to a fifth aspect, the invention relates to a method for estimating deterioration of a steel support structure supporting an offshore wind turbine, said steel support structure being made of a first type of steel, said method comprising the steps of:
(a) providing a second sensor, said second sensor comprising a Zn reference electrode;
(b) embedding said second sensor in connection with said steel support structure;
(c) estimating the degree of corrosion of the steel support structure by measuring the local electrical potential using said Zn reference electrode.

According to a sixth aspect the invention relates to a system comprising a steel support structure supporting a wind turbine, a control unit, and a first sensor, wherein:
said steel support structure is made of a first type of steel;
said first sensor have one or more sensor elements, wherein a first sensor element of said one or more sensor elements is made of a type of steel corresponding to said first type of steel;
said first sensor is arranged in connection with said steel support structure;
said first sensor is configured to induce an electrical current through at least one of said one or more sensor elements;
said system is configured to monitor the deterioration of a part of said first sensor by in a first time interval measure electrical properties of the first sensor and store the measurements as first data; and said system is configured to process said first data using said processing unit to estimate the deterioration of said steel support structure.

The different aspects of the present invention can be implemented in different ways as described above and in the following, each yielding one or more of the benefits and advantages described in connection with at least one of the aspects described above, and each having one or more preferred embodiments corresponding to the preferred embodiments described in connection with at least one of the aspects described above and/or disclosed in the dependant claims. Furthermore, it will be appreciated that embodiments described in connection with one of the aspects described herein may equally be applied to the other aspects.

BRIEF DESCRIPTION OF THE DRAWINGS

The above and/or additional objects, features and advantages of the present invention, will be further elucidated by the following illustrative and non-limiting detailed description of embodiments of the present invention, with reference to the appended drawings, wherein.

DETAILED DESCRIPTION

In the following description, reference is made to the accompanying figures which show by way of illustration how the invention may be practiced.

Figure 1:
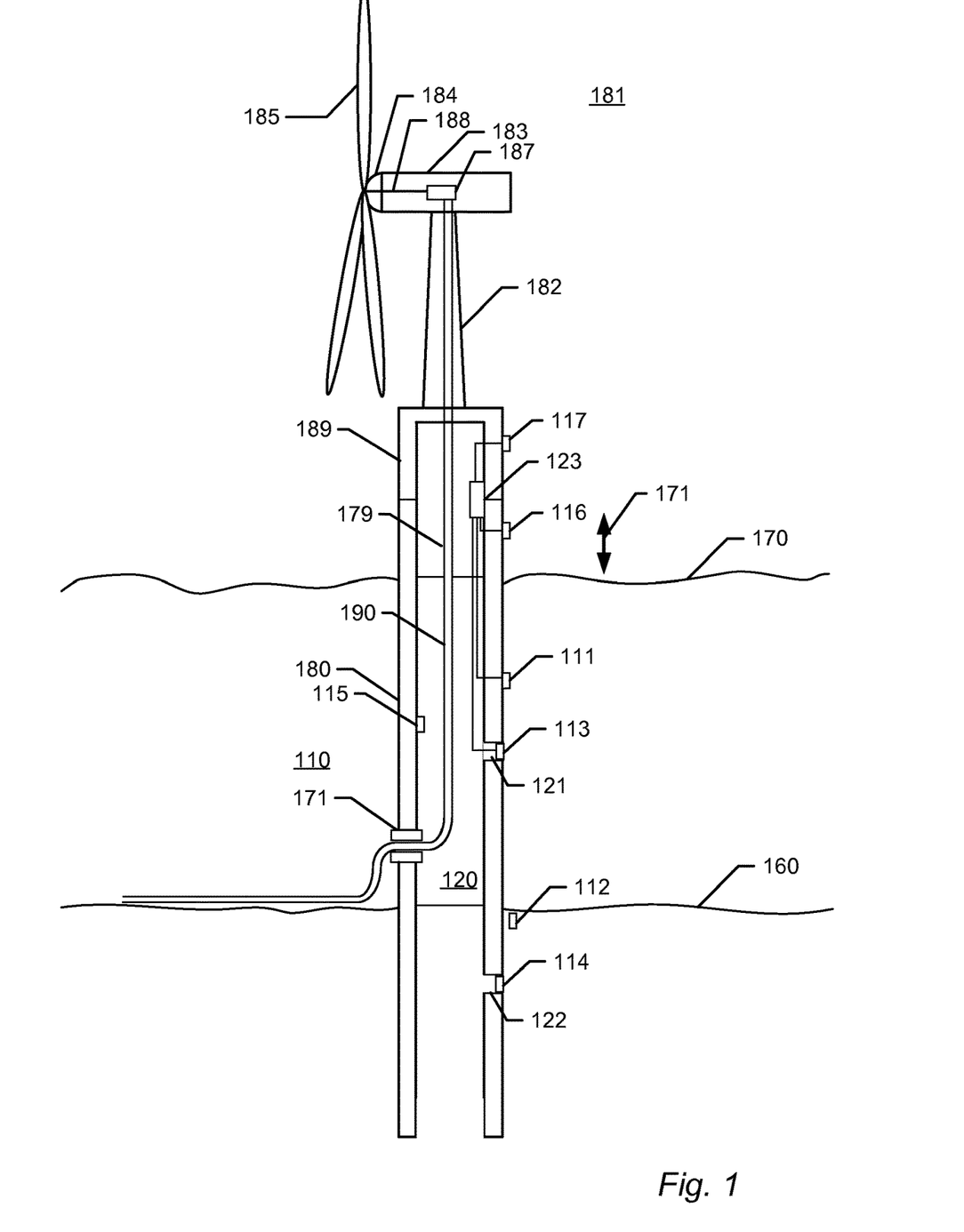
FIG. 1 shows a schematic drawing of an offshore wind turbine arranged on a steel support structure, with a plurality of sensors arranged in connection with the steel support structure according to an embodiment of the present invention.

FIG. 1 shows a schematic drawing of an offshore wind turbine 181 arranged on a steel support structure 180, with a plurality of sensors 111-117 arranged in connection with the steel support structure 180 according to an embodiment of the present invention. The wind turbine 181 is a horizontal-axis wind turbine. The wind turbine 181 comprises a tower 182, a nacelle 183, and a rotor hub 184 connected to three rotor blades 185. The rotor blade/rotor hub assembly is connected to a shaft 188 that drives a generator 187. The generator 187 generates electric energy that is provided to the grid via an electric cable 190. The steel support structure 180 is partly submerged in water 170 and partly embedded into the seabed 160. The steel support structure comprises a transition piece 189. The electrical cable 190 may be guided using a guiding device 171 e.g. a j-tube, into a hollow interior 120 of the steel support structure 180 from the exterior water 110. The steel support structure 180 is in this embodiment a monopile structure.

A first sensor 111 is attached to the outside of steel support structure 180 below the sear surface, a second sensor 112 is embedded into the seabed close to the steel support structure 180, a third sensor 113 is arranged in a first opening 121 of the steel support structure 180, a fourth sensor 114 is arranged in a second opening 122 of the steel support structure 180, a fifth sensor 115 is attached to the inside of the steel support structure 180, a sixth sensor 116 is attached to the outside of the steel support structure in the tidal/splash or atmospheric zone 171, a seventh sensor 117 is attached to the transition piece 181 of the steel support structure in the tidal/splash or atmospheric zone.

The first and second opening 121 and 122 form a passage from the hollow interior 120 to the exterior 110. The first opening 121 is formed in the part of the steel support structure 180 submerged in water and the second opening 122 is formed in the part of the steel support structure 180 embedded in the seabed 160.

The first sensor 111, the third sensor 113, the sixth sensor 116, and the seventh sensor 117 are connected to a central control unit 123 via power and/or control cables. The cables may enter the interior of the steel support structure 180 through small holes drilled in the steel support structure 180. The first sensor 111, the third sensor 113, the sixth sensor 116, and the seventh sensor 117 may receive power from the central control unit 123 and transmit recorded data to the central control unit 123 via the cables. The second sensor 112, the fourth sensor 114, and the fifth sensor 115 each comprise a battery providing power. The second sensor 112, the fourth sensor 114, and the fifth sensor 115 may further comprise a wireless communication unit configured to transmit recorded data to the central control unit 123 or another control unit. The second sensor 112, the fourth sensor 114, and the fifth sensor 115 may further comprise a memory unit configured to store the data generated by the sensors. In other embodiments all sensors may be connected via power and/or control cables.

Figure 2:
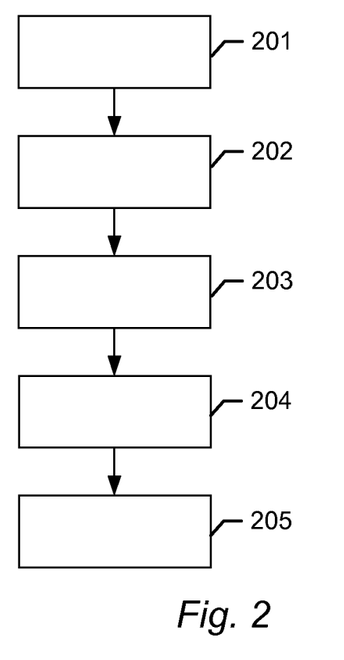
FIG. 2 shows a flowchart of a method for estimating deterioration of a steel support structure supporting an offshore wind turbine made of a first type of steel according to an embodiment of the invention.

FIG. 2 shows a flowchart of a method for estimating deterioration of a steel support structure supporting an offshore wind turbine made of a first type of steel according to an embodiment of the invention. In the first step 201, a first sensor is provided having one or more sensor elements, wherein a first sensor element of the one or more sensor elements is made of a type of steel corresponding to the first type of steel. In the next step, 202, the first sensor is arranged in connection with the steel support structure. Then in step 203, an electrical current is induced through at least one or more sensor elements of the first sensor. Next in step 204, deterioration of a part of the first sensor is monitored in a first time interval by measuring electrical properties of the first sensor and storing the measurements as first data. Finally, in step 204 the deterioration of the steel support structure is estimated from the first data.

Figure 3:
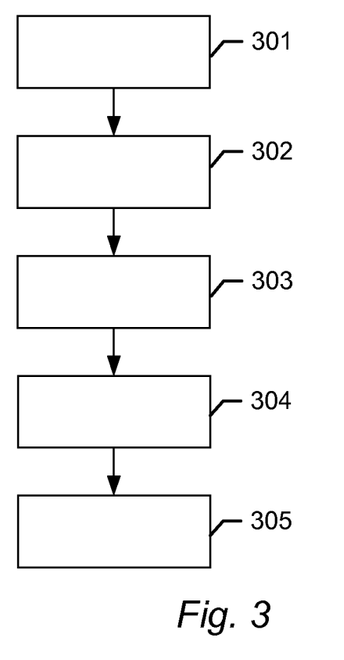
FIG. 3 shows a flowchart of a method for estimating deterioration of a steel support structure supporting an offshore wind turbine according to an embodiment of the invention.

FIG. 3 shows a flowchart of a method for estimating deterioration of a steel support structure supporting an offshore wind turbine according to an embodiment of the invention. The steel support structure is in this embodiment coated on a first surface with a first type of coating. In the first step 301, a first sensor is provided having one or more sensor elements, wherein a first sensor element of the one or more sensor elements is made of a metal and coated with the first type of coating. In the next step 302, the first sensor is arranged in connection with the steel support structure. Then in step 303, an electrical current is induced though the first sensor element. Next in step 304, the deterioration of the coating of the first sensor element is monitored in a first time interval by measuring electrical properties of the first sensor element and storing the measurements as first data. Finally, in step 305, the deterioration of the coating of the steel support structure is estimated from the first data.

Figure 4:
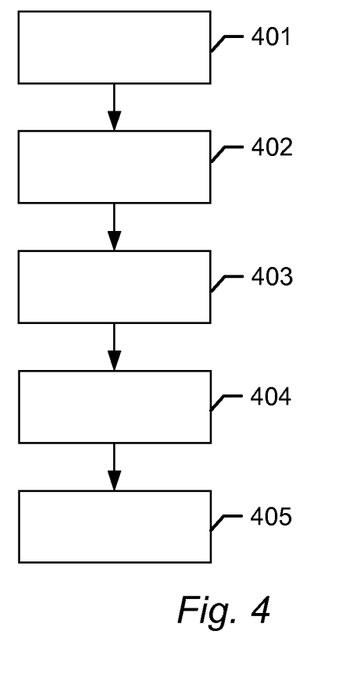
FIG. 4 shows a flowchart of a method for estimating deterioration of a steel support structure supporting an offshore wind turbine according to an embodiment of the invention.

FIG. 4 shows a flowchart of a method for estimating deterioration of a steel support structure supporting an offshore wind turbine according to an embodiment of the invention. The steel support structure has a wall surrounding a hollow interior and the wall has a first opening forming a passage from the hollow interior to the exterior. In the first step 401, a first sensor is provided having one or more sensor elements, wherein a first sensor element of the one or more sensor elements is made of a metal. In the next step 402, the first sensor is arranged in the first opening of the steel support structure. Next in step 403, an electrical current is induced through at least one of the one or more sensor elements. Next in step 404, the deterioration of a part of the first sensor is monitored by in a first time interval measuring electrical properties of the first sensor and storing the measurements as first data. Finally, in step 405, the deterioration of the steel support structure is estimated from the first data.

Figure 5:
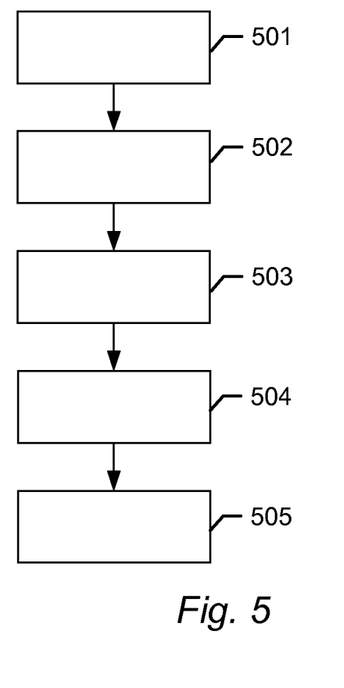
FIG. 5 shows a flowchart of a method for estimating deterioration of a steel support structure supporting an offshore wind turbine according to an embodiment of the present invention.

FIG. 5 shows a flowchart of a method for estimating deterioration of a steel support structure supporting an offshore wind turbine according to an embodiment of the present invention. In the first step 501, a first sensor is provided comprising a first sensor element, a second sensor element, a first electrical insulator, and a second electrical insulator. The first sensor element is made of a metal; the second sensor element is separated from the first sensor element by the first electrical insulator; the second electrical insulator and the first sensor element together encapsulate the second sensor element and the first electrical insulator and protect the second sensor element and the first electrical insulator from coming into contact with the water. The first electrical insulator is configured to either breakdown, dissolve, and/or lower its electrical impedance when it comes into contact with water, whereby the electrical impedance between the first sensor element and the second sensor element is lowered after corrosion has formed a pinhole in the first sensor element allowing the water to come into contact with the first electrical insulator. In the next step 502, the first sensor is arranged in connection with the steel support structure. Then in step 503, an electrical current is induced through the first sensor element and/or the second sensor element. Next in step 504, the deterioration of the first sensor element is monitored in a first time interval by measuring electrical properties of the first sensor and storing the measurements as first data. Finally, in step 505, the deterioration of the steel support structure is estimated from the first data by processing the first data to estimate the point in time T3 when a pinhole is formed in the first sensor element.

FIGS. 6a-b show schematic drawings of a sensor 601 arranged on a wall 680 of a steel support structure supporting an offshore wind turbine, according to an embodiment of the invention. FIG. 6a shows a front view and FIG. 6b shows a cross section taken along the line 699. Only a small part of the wall 680 is shown. The sensor 601 is an electrical resistance corrosion sensor. The sensor 601 comprises a first sensor element 602 and a reference sensor element 603. The first sensor element is made of a metal. The first sensor element 602 and the steel support structure may be made the same type of steel. The first sensor element 602 and the reference sensor element 603 are preferably made of the same material. The reference sensor element 603 is used as a temperature sensor. The reference sensor element 603 is encapsulated by the housing of the sensor 601 and thereby protected from the corrosive environment. The first sensor element 602 is exposed to a corrosive environment and becomes thinner over time as a result of the corrosion. The thickness 682 of the first sensor element 602 may be estimated using the below equation:

$$d = \rho(T)\frac{L}{W \cdot R} \qquad (1)$$

where d is the thickness 682 of the first sensor element 602, $\rho(T)$ is the resistivity of the material of the first sensor element 602 at the temperature T, L is the length 683 of the first sensor element 602, W is the width 681 of the first sensor element 602, and R is the resistance of the first sensor element.

Figure 7:
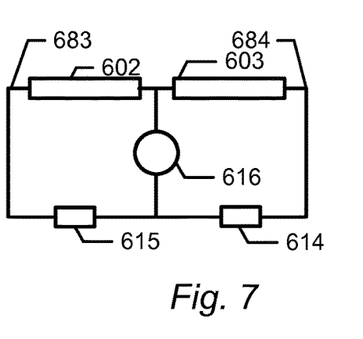
FIG. 7 shows an electrical circuit that may be used in the sensor shown in FIG. 6 according to an embodiment of the invention.

Thus, by measuring the temperature and the resistivity of the first sensor element at a plurality of points in time the absolute corrosion and the rate of corrosion may be estimated. FIG. 7 shows an electrical circuit that may be used in the first sensor 601. A current source 616 provides a current that is induced through the first sensor element 602 and the reference sensor element 603. Two resistors 615 and 614 are provided. The two resistors 614 and 615 preferably have an electrical resistance substantially higher than the electrical resistance of the first sensor element 602 and the reference sensor element 603. This ensures that the current induced through the first sensor element 602 is only influenced to a small degree by the corrosion of the first sensor element 602. To estimate the thickness 682 of the first sensor element 602, the resistance of the first sensor element 602 and the reference sensor element 603 may be calculated based on measured voltages across 602 and 603. The sensor 601 can only determine the average corrosion of the first sensor element 602 e.g. the sensor 601 cannot determine the degree of pitting corrosion.

Figure 8A:
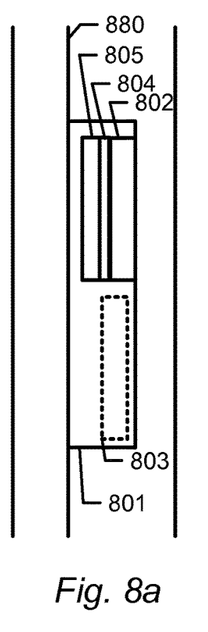
FIGS. 8a-d show central cross-sections of a sensor arranged on a wall of a steel support structure supporting an offshore wind turbine, according to an embodiment of the invention.
Figure 8B:
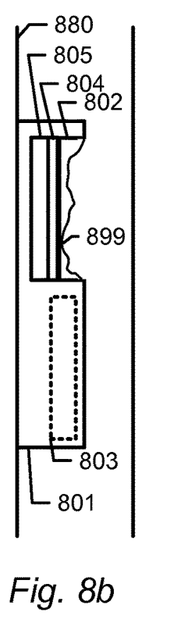
Figure 8C:
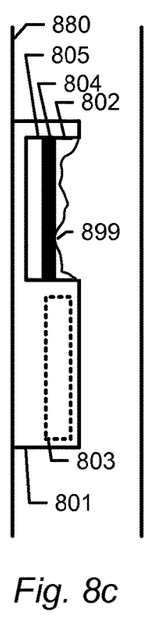
Figure 8D:
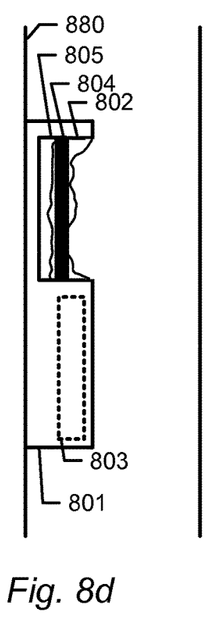

FIGS. 8a-d show central cross-sections of a sensor 801 arranged on a wall 880 of a steel support structure supporting an offshore wind turbine, according to an embodiment of the invention. The sensor 801 is configured to estimate pitting corrosion. The sensor 801 may have outer dimension similar to the outer dimension of the sensor 601 shown in FIGS. 6a-b. The sensor 801 is shown at different points in time (p1, p2, p3, p4), where FIG. 8a shows the sensor at p1 being immediately after the sensor 801 has been arranged on the wall 880, FIG. 8b shows the sensor 801 at p2 being after p1, FIG. 8c shows the sensor 801 at p3 being after p2, and FIG. 8d shows the sensor 801 at p4 being after p3. The sensor 801 comprises a first sensor element 802 made of a metal, a second sensor element 805, a first electrical insulator 804, and a second electrical insulator. In this embodiment, the housing of the sensor 801 constitutes the second electrical insulator. The second sensor element 805 may also be made of a metal. The second sensor element 805 is separated from the first sensor element 802 by the first electrical insulator 804. In this embodiment, the first sensor element 802, the second sensor element 805 and the first electrical insulator 804 are planar elements that may have a width and a length similar to the width 681 and length 683 of the first sensor element 602 shown in FIG. 6a i.e. they may have a width and length being substantially equal. The second electrical insulator and the first sensor element 802 together encapsulate the second sensor element 805 and the first electrical insulator 804 and protect the second sensor element 805 and the first electrical insulator 804 from coming into contact with the water (until corrosion has formed a hole in the first element 801). The first electrical insulator 804 is configured to either breakdown, dissolve, and/or lower its electrical impedance when it comes into contact with water, whereby the electrical impedance between the first sensor element 802 and the second sensor element 805 is lowered after corrosion has formed a pinhole in the first sensor element 802 allowing water to come into contact with the first electrical insulator 804. As an example, the first electrical insulator 804 may be a piece of paper. At p1 the corrosion processes have not started and all elements of the sensor 801 are intact. At p2 the first sensor element 802 starts to corrode. In this example, the corrosion is non-uniform and a pit 899 is formed. At this point in time the pit 899 has not formed a pinhole, thus the first electrical insulator 804 and the second sensor element are intact since they both still are encapsulated and protected by the housing of the sensor (the second electrical insulator) and the first sensor element 802. At p3 the pit 899 has resulted in the formation of a pinhole (the first sensor element has corroded through locally) whereby the first electrical insulator 804 comes into contact with the water electrolyte and either breaks down, dissolves, and/or lower its electrical impedance. As an example, if the first electrical insulator is a piece of paper, the paper will be wetted by the seawater flowing through the pinhole whereby the electrical impedance of the paper will be lowered.

After a pinhole has been formed in the first sensor element 802 and water comes into contact with the second sensor 805 element three effects may result.

Figure 9:
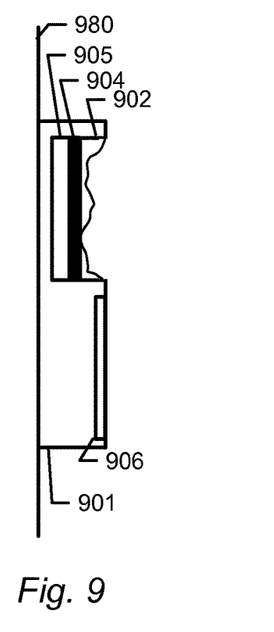
FIG. 9 shows central cross-sections of a sensor arranged on a wall of a steel support structure supporting an offshore wind turbine, according to an embodiment of the invention.

Firstly, the impedance between the second sensor element 805 and a reference electrode separated from the second sensor element 805 at least by the first electrical insulator 804, will decrease as the insulating properties of the first electrical insulator 804 will decrease. The first sensor element 802 may function as the reference electrode. Alternatively, the first sensor 901 may comprise a dedicated reference electrode 906, as shown in FIG. 9.

Secondly, the second sensor element 805 will start to corrode, as shown in FIG. 8d. This corrosion may be determined by measuring an increase in the impedance of the second sensor element, i.e. similar to how the corrosion of the first sensor element 602 is estimated as explained in relation to FIGS. 6a-b.

Thirdly, the impedance between a first electrical terminal connected to a first end of the first sensor element 802 and a second electrical terminal 802 connected to a second end of the first sensor element will fall immediately after the pinhole has been formed as the first electrical insulator 804 will provide an electrolytical contact.

Thus, the sensor 801 may comprise electrical circuitry configured to periodically measure the impedance between the second sensor element 805 and a reference electrode, the impedance of the second sensor element 805, and/or the impedance of the first sensor element 802 and store the measurements as first data. A processing unit of the sensor 801 or a processing unit having access to the first data may estimate the point in time T3 when a pinhole was formed in the first sensor element 802 by processing the first data by detecting an increase and/or decrease in the /impedance as explained above. The sensor 801 may optionally further comprise a temperature sensor 803, and be configured to estimate the average corrosion of the first sensor element 802 e.g. as explained in relation to FIGS. 6-7. This enables a relative measure of the degree of pitting corrosion to be determined from the equation below:

$$PF = \frac{d\_p}{d\_i}$$

where PF is the relative measure, d_i is the initial thickness of the first sensor element 802 and d_p is the average height of the first sensor element at T3.

Thus, PF is a number between 0 and 1, where the 0 means that the corrosion is perfectly uniform and no pitting corrosion is present, and 1 means that only pitting corrosion has occurred. In practice, PF can never become 1 since the formation of a pit will result in a decrease in the average height of the first sensor element 802.

FIGS. 10a-e show a central cross-section of a sensor 1001 arranged on a wall 1080 of a steel support structure supporting an offshore wind turbine, according to an embodiment of the invention. In this embodiment the wall of the steel support structure is coated 1079 on a first surface with a first type of coating. Only a small part of the wall 1080 is shown. The sensor 1001 comprises a first sensor element 1002 and a reference electrode 1006. The sensor 1001 is configured to estimate the electrical voltage/impedance between the first sensor element 1002 and the electrode 1006. The reference electrode 1006 may be a structure connection. The sensor 1001 may be configured to measure the a DC voltage between the first sensor element 1002 and the reference electrode 1006 The Zn reference electrode may be especially suitable if the sensor 1001 is embedded in the seabed. In this embodiment, the first sensor element 1002 is a planar element that may have a width and a length similar to the width 681 and length 683 of the first sensor element 602 shown in FIG. 6a.

The first sensor element 1002 is made of a metal. The first sensor element 1002 and the steel support structure may be made the same type of steel. The first sensor element 1002 is coated with the first type of coating, i.e. the steel support structure and the first sensor element 1002 are coated with the same type of coating. The sensor 1001 is configured to induce an electrical current 1008 between the first sensor element 1002 and the reference electrode 1006 through the water or the seabed and estimate the electrical impedance/resistance between the first sensor element 1002 and the reference electrode 1006. The sensor 1001 may be configured to estimate the electrical impedance/resistance between the first sensor element 1002 and the reference electrode 1006 by using a suitable electrical circuit such as Wheatstone's bridge or the like. The impedance/resistance is influenced by the thickness/state of the coating 1007, the electrical conductivity of the exterior environment (seabed or water) and the electrical conductivity of the coating 1007. The electrical conductivity of the exterior environment (seabed or water) and the electrical conductivity of the coating 1007 are both relatively stable, thus the estimated impedance/resistance is a good indicator of the thickness/state of the coating and may typically drop over time as shown in FIG. 11 as a result of deterioration of the coating 1007. The sensor 1001 may further optionally comprise a temperature sensor 1003 (only shown in FIG. 10e). The temperature sensor may allow the sensor 1001 to take account of temperature dependent changes in the electrical conductivity of the exterior environment (seabed or water) and the electrical conductivity of the coating 1007 whereby the impedance/resistance may be estimated at a particular reference temperature e.g. approximately the yearly average temperature of the exterior environment.

Figure 10A:
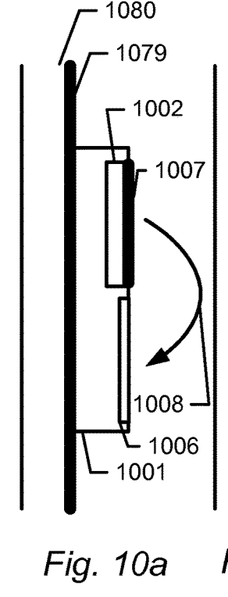
FIGS. 10a-e show a central cross-section of a sensor arranged on a wall of a steel support structure supporting an offshore wind turbine, according to an embodiment of the invention.
Figures 10B, 10C, 10D:
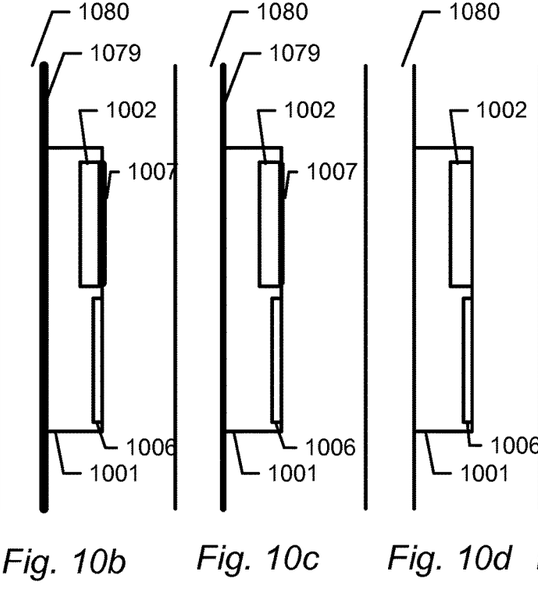
Figure 10E:
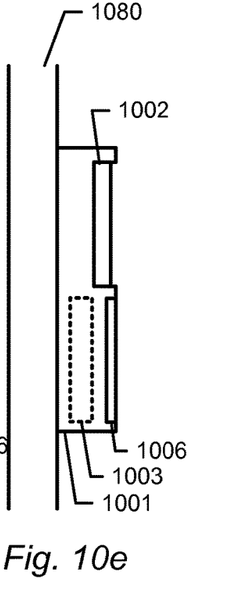
Figure 11:
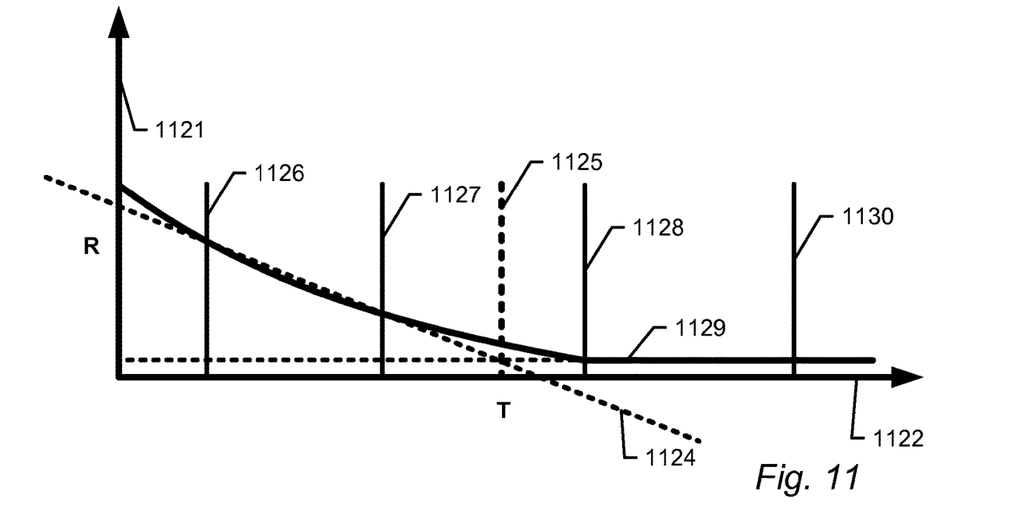
FIG. 11 shows an example of a function of the electrical impedance/resistance between the first sensor element and the reference electrode over time.

The sensor 1001 is shown at different points in time (p1, p2, p3, p4, p5), where FIG. 10a shows the sensor at p1 being immediately after the sensor 1001 has been arranged on the wall 1080, FIG. 10b shows the sensor 1001 at p2 being after p1 where the coating is slightly deteriorated, FIG. 10c shows the sensor 1001 at p3 being after p2 where the coating is heavily deteriorated, FIG. 10d shows the sensor 1001 at p4 being after p3 where the function of the coating has stopped working, and FIG. 10e shows the sensor 1001 at p5 being after p4.

FIG. 11 shows an example of a function 1129 of the electrical impedance/resistance between the first sensor element 1002 and the reference electrode 1006 over time, where the axis 1122 represents time and the axis 1121 represents the impedance/resistance. The vertical line 1126 corresponds to p2, the vertical line 1127 corresponds to p3, the vertical line 1128 corresponds to p4, and the vertical line 1130 corresponds to p5. The impedance/resistivity drops until the coating has been completely broken down or lost its ability to function as insulator. After the coating has been broken down/lost insulating ability at p4 the impedance/resistivity stays at an approximately constant level determined by the electrical conductivity of the water plus what remains of the coatings ability to provide insulation or the seabed plus what remains of the coatings ability to provide insulation dependent on where the sensor 1001 is used.

The sensor 1001 may be configured to estimate the electrical impedance/resistance between the first sensor element 1002 and the reference electrode 1006 at a plurality of point in time and store the estimate as first data. The first data may be processed to estimating the deterioration of the coating of the steel support structure 1079. The first data may be processed to estimate the point in time (T1) where the coating has deteriorated to a particular point. The particular point may be an absolute parameter value or a relative parameter value. The parameter value may be indicative of the coating's ability to protect against corrosion. The particular point may be when the coating has stopped to protect the steel support structure against corrosion or only has a particular percentage of its original protective capabilities left. A curve fit may be used to find T1 e.g. a curve may be fitted to the first data and used to predict T1.

FIG. 11 illustrates a simple example, where a linear curve fit 1124 is applied to the electrical impedances/resistances estimated at p2 and p3 to predict the point in time where the coating has stopped to protect the steel support structure against corrosion. There is in this example a relative large discrepancy between the prediction 1125 and actual point in time 1128. A better prediction may result if a more correct curve is used for the curve fit e.g. an exponential curve or if more data points are used. A suitable curve fit may be found by evaluating empirical values from previous sensors.

Figure 12:
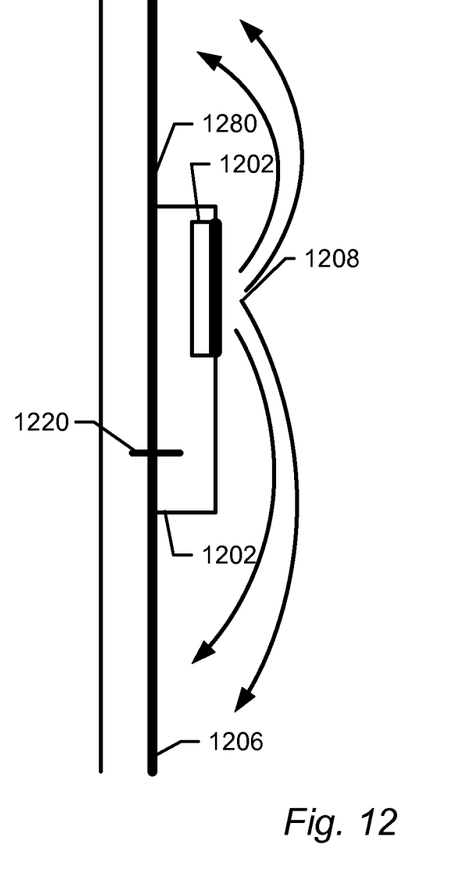
FIG. 12 shows a central cross-section of a sensor arranged on a wall of a steel support structure supporting an offshore wind turbine, according to an embodiment of the invention.

FIG. 12 shows a central cross-section of a sensor 1201 arranged on a wall 1280 of a steel support structure supporting an offshore wind turbine, according to an embodiment of the invention. The sensor 1201 comprises a first sensor element 1202 and is electrically connected to the wall of the steel support structure. Thus in this embodiment, the metal 1280 of the steel support structure functions as a reference electrode 1206. The sensor 1201 is configured to estimate the electrical impedance/resistance between the first sensor element 1202 and the reference electrode 1206 similar to the sensor disclosed in relation to FIGS. 10a-e.

Although some embodiments have been described and shown in detail, the invention is not restricted to them, but may also be embodied in other ways within the scope of the subject matter defined in the following claims. In particular, it is to be understood that other embodiments may be utilised and structural and functional modifications may be made without departing from the scope of the present invention.

In device claims enumerating several means, several of these means can be embodied by one and the same item of hardware. The mere fact that certain measures are recited in mutually different dependent claims or described in different embodiments does not indicate that a combination of these measures cannot be used to advantage.

It should be emphasized that the term "comprises/comprising" when used in this specification is taken to specify the presence of stated features, integers, steps or components but does not preclude the presence or addition of one or more other features, integers, steps, components or groups thereof.

The invention claimed is:

1. A method for estimating deterioration of a steel support structure supporting an offshore wind turbine, said steel support structure being made of a first type of steel and is coated on a first surface with a first type of coating, said method comprising:
   providing a first sensor having one or more sensor elements, wherein a first sensor element of said one or more sensor elements is made of metal and is coated with said first type of coating;
   arranging said first sensor in connection with said steel support structure;
   inducing an electrical current between said first sensor element and a reference electrode through water or the seabed;
   monitoring, in a first time interval, the deterioration of said first sensor element by measuring an electrical impedance between the first sensor element and the reference electrode and storing the measurements as first data; and
   estimating the deterioration of said coating of said steel support structure from said first data, wherein estimating the deterioration comprises analyzing the first data to estimate a change over time of the electrical impedance between the first sensor element and the reference electrode.

2. A method according to claim 1, wherein estimating the deterioration further comprises estimating a first point in time (T1) where the coating has deteriorated to a particular point.

3. A method according to claim 2, further comprising applying additional anti-corrosion protection to said steel support structure at a second point in time (T2) where T2 is selected dependent on T.

4. A method according to claim 3, wherein the anti-corrosion protection is a cathodic protection system.

5. A method according to claim 3, wherein the anti-corrosion protection is a new coating or repairs one or more existing coatings.

6. A method according to claim 1, further comprising:
providing a second sensor, said second sensor comprising a Zn reference electrode; and
embedding said second sensor in the seabed.

7. A method according to claim 1, wherein the steel support structure comprises a wall surrounding a hollow interior and wherein the steel support structure comprises a first opening in the wall forming a passage from the hollow interior to an exterior of the steel support structure and wherein the first sensor is arranged in the first opening.

8. method according to claim 7, wherein the first sensor is arranged inside the first opening in a manner whereby no part of the first sensor extends out of the first opening and into the exterior.

9. A method according to claim 8, wherein the first sensor is arranged inside the first opening before the steel support structure has been secured to the seabed, the first opening being formed in a part of the steel support structure that is inserted into the seabed, and wherein the steel support structure is subsequently secured to the seabed whereby the first sensor is arranged in the seabed and can provide measurements indicative of deterioration of the part of the steel support structure inserted into the seabed.

10. A method according to claim 7, wherein the first sensor is secured to a fixation element, and wherein the fixation element is inserted into the first opening.

11. A method according to claim 10, wherein a plurality of sensors are secured to the fixation element.

12. A method according to claim 7, wherein the first opening and the fixation element have a circular or oval shape.

13. A method according to claim 7, wherein the first sensor element faces the exterior and one or more power or control cables are connected to the first sensor, the one or more power or control cables being arranged inside the hollow interior of the steel support structure.

14. A method according to claim 13, wherein the one or more power or control cables are connected to the first sensor before the steel support structure is secured to the seabed, and wherein a protective element protrudes from the inner wall of the hollow interior below the first opening, said protective element being configured to protect the one or more power or control cables when the steel support structure is inserted into the seabed.

15. A method according to claim 1, wherein the steel support structure functions as the reference electrode, the electrical current is induced between said first sensor element and the steel support structure, and the electrical impedance between the first sensor element and the steel support structure is measured.

16. A method for estimating deterioration of a steel support structure supporting an offshore wind turbine, said steel support structure being made of a first type of steel, said method comprising:

providing a first sensor having one or more sensor elements wherein a first sensor element of said one or more sensor elements is made of metal, wherein said first sensor further comprises a second sensor element, a first electrical insulator, and a second electrical insulator, wherein said second sensor element is separated from said first sensor element by said first electrical insulator; said second electrical insulator and said first sensor element together encapsulate said second sensor element and the first electrical insulator and protect the second sensor element and the first electrical insulator from coming into contact with the water; and wherein said first electrical insulator is configured to either breakdown, dissolve, and/or lower its electrical impedance when it comes into contact with water, whereby the electrical resistance/impedance between the first sensor element and the second sensor element is lowered after corrosion has formed a pinhole in the first sensor element allowing the water to come into contact with the first electrical insulator;

arranging said first sensor in connection with said steel support structure;

inducing an electrical current through at least one of said one or more sensor elements;

monitoring, in a first time interval, the deterioration of said first sensor element by measuring electrical properties of the first sensor and storing the measurements as first data; and estimating the deterioration of said steel support structure from said first data, wherein estimating the deterioration comprises processing said first data to estimate a point in time (T3) when a pinhole was formed in the first sensor element.

17. A method according to claim 16, wherein monitoring the deterioration comprises measuring, at a plurality of points in time, one or more of:

an electrical impedance of the second sensor element;

an electrical impedance between the second sensor element and a reference electrode separated from the second sensor element at least by the first electrical insulator; or an electrical impedance between a first electrical terminal connected to a first end of the first sensor element and a second electrical terminal connected to a second end of the first sensor element, wherein T3 is estimated by processing the electrical impedance at the plurality of points in time.

18. A method according to claim 16, wherein T3 is estimated as a point in time where the electrical impedance or an estimated rate of change of the electrical impedance reaches or exceeds a predetermined threshold.

19. A system comprising a steel support structure supporting a wind turbine, a processing unit, and a first sensor, wherein:

said steel support structure is made of a first type of steel and is coated on a first surface with a first type of coating;

said first sensor have one or more sensor elements, and wherein a first sensor element of said one or more sensor elements is made of metal and is coated with said first type of coating;

said first sensor is arranged in connection with said steel support structure;

said first sensor is configured to induce an electrical current between said first sensor element and a reference electrode through water or the seabed;

said system is configured to monitor, in a first time interval, the deterioration of said first sensor element by measuring an electrical impedance between the first sensor element and the reference electrode and storing the measurements as first data; and said system is configured to process said first data using said processing unit to estimate the deterioration of said coating of said steel support structure wherein estimating the deterioration comprises analyzing the first data to estimate a change over time of the electrical impedance between the first sensor element and the reference electrode.

20. A system comprising a steel support structure supporting a wind turbine, a processing unit, and a first sensor, wherein:

said steel support structure is made of a first type of steel;

said first sensor have one or more sensor elements, and wherein a first sensor element of said one or more sensor elements is made of metal, wherein said first sensor further comprises a second sensor element, a first electrical insulator, and a second electrical insulator, wherein said second sensor element is separated from said first sensor element by said first electrical insulator; said second electrical insulator and said first sensor element together encapsulate said second sensor element and the first electrical insulator and protect the second sensor element and the first electrical insulator from coming into contact with the water; and wherein said first electrical insulator is configured to either breakdown, dissolve, and/or lower its electrical impedance when it comes into contact with water, whereby the electrical resistance/impedance between the first sensor element and the second sensor element is lowered after corrosion has formed a pinhole in the first sensor element allowing the water to come into contact with the first electrical insulator;

said first sensor is arranged in connection with said steel support structure;

said first sensor is configured to induce an electrical current through at least one of said one or more sensor elements;

said system is configured to monitor, in a first time interval, the deterioration of said first sensor element by measuring electrical properties of the first sensor and storing the measurements as first data; and said system is configured to process said first data using said processing unit to estimate the deterioration of said steel support structure, wherein estimating the deterioration comprises processing said first data to estimate a point in time (T3) when a pinhole was formed in the first sensor element.

* * * * *